US006553812B2

(12) United States Patent  (10) Patent No.: US 6,553,812 B2
Park et al.  (45) Date of Patent: Apr. 29, 2003

(54) COMBINED OIL QUALITY AND VISCOSITY SENSING SYSTEM

(75) Inventors: Kyong M. Park, Thousand Oaks, CA (US); Marcos A. Nassar, Los Angeles, CA (US)

(73) Assignee: Kavlico Corporation, Moorpark, CA (US)

( * ) Notice: Subject to any disclaimer, the term of this patent is extended or adjusted under 35 U.S.C. 154(b) by 13 days.

(21) Appl. No.: 09/954,674

(22) Filed: Sep. 17, 2001

(65) Prior Publication Data

US 2002/0011095 A1 Jan. 31, 2002

Related U.S. Application Data

(63) Continuation-in-part of application No. 09/563,470, filed on May 2, 2000, now abandoned.

(51) Int. Cl.[7] ............... B60Q 1/00; G01N 11/00; G01N 33/30; G01N 31/00; G08B 21/00
(52) U.S. Cl. ............... 73/54.01; 73/53.05; 73/54.05; 324/663; 324/71.1; 422/82.01; 702/52; 340/631
(58) Field of Search ............... 73/54.01, 54.02, 73/54.05, 53.01, 61.73, 53.05; 324/698, 71.1, 663; 422/82.01, 82.13; 702/52; 340/631

(56) References Cited

U.S. PATENT DOCUMENTS

| 3,086,386 A | * | 4/1963 | Kapff ................ 73/23.2 |
| 3,115,768 A | * | 12/1963 | Rhodes et al. ............ 73/54.05 |
| 4,345,202 A | * | 8/1982 | Nagy et al. ............ 324/58.5 B |
| 4,733,556 A | * | 3/1988 | Meitzler et al. ............ 73/54.01 |
| 4,876,882 A | * | 10/1989 | Yau ............ 73/54.01 |
| 4,926,682 A | * | 5/1990 | Holm-Kennedy et al. . 73/54.01 |
| 5,279,149 A | * | 1/1994 | Williams et al. ............ 73/54.01 |
| 5,377,531 A | * | 1/1995 | Gomm ............ 73/53.05 |
| 5,435,170 A | * | 7/1995 | Voelker et al. ............ 73/53.05 |
| 5,540,086 A | * | 7/1996 | Park et al. ............ 73/53.05 |
| 5,604,441 A | * | 2/1997 | Freese et al. ............ 324/663 |
| 5,889,200 A | * | 3/1999 | Centers et al. ............ 73/53.01 |
| 5,929,754 A | * | 7/1999 | Park et al. ............ 340/439 |
| 5,968,371 A | * | 10/1999 | Verdegan et al. ............ 210/739 |
| 6,459,995 B1 | * | 10/2002 | Collister ............ 702/23 |

* cited by examiner

*Primary Examiner*—Helen Kwok
*Assistant Examiner*—David J. Wiggins
(74) *Attorney, Agent, or Firm*—Oppenheimer Wolff & Donnelly LLP

(57) ABSTRACT

A combined oil quality and fuel contamination sensing system includes a capacitive dielectric sensor and pressure sensing arrangements for measuring the dielectric constant of the oil and the pressure of the oil, respectively, with the oil pressure being indicative of oil viscosity and contamination. The sensors take measurements as oil flows through an internal combustion engine and provide an indication of the cause of a problem with oil in an engine. The system may also include a microcomputer and circuitry for generating an indication of dielectric constant and circuitry for generating an indication of the presence of contaminants within the engine. The system may also include an additional sensor measuring the temperature of oil within the system to adjust oil dielectric constant and viscosity indications. The capacitive dielectric sensor constitute the principal restriction in the flow path between an input high pressure sensing port and an outlet low pressure port.

17 Claims, 2 Drawing Sheets

COMBINED OIL QUALITY AND VISCOSITY SENSING SYSTEM

RELATED PATENT APPLICATIONS

The application is a continuation-in-part of U.S. patent application Ser. No. 09/563,470 filed May 2, 2000, now abandoned.

BACKGROUND OF THE INVENTION

1. Field of the Invention

The present invention relates to an oil quality and viscosity sensing system, and more particularly, pertains to an oil quality evaluation system employing arrangements for detecting fuel leakage into the oil.

2. Description of the Related Art

One of the most important factors that contributes to the efficiency and durability of internal combustion engines is lubrication. As engine oil "breaks down" it is less effective in protecting an engine from damage caused by friction between engine parts. More specifically, the normal life span of motor oils is limited by thermal breakdown, additive depletion and carbon particulates that result from the combustion process.

The deterioration of engine oil is marked by a decrease in the viscosity of the oil. The dielectric constant of engine oil provides an indication of the deterioration of the oil or lack thereof. It is known that the dielectric constant of the lubricating oil, in internal combustion engines for example, increases with oil deterioration during operation of the invention. The dielectric constant of motor oil is typically between 1.6 and 3.2 depending upon its brand and age. For example, the dielectric constant of a particular brand of motor oil may increase from 2.19 to 2.35 after 400 hours of use in a particular internal combustion engine under certain operating conditions. Thus, it is desirable to have an indication of when engine oil has deteriorated to the point where it should be changed. By measuring the dielectric constant of the motor oil, it may be determined when such a change should occur.

Premature lubrication failure can also result from the presence of contaminants in the engine oil such as coolant (glycol ethylene), fuel or water. The presence of these contaminants in motor oil is often indicative of a mechanical failure such as a damaged head gasket or a broken piston ring. Thus, it is also desirable to have arrangements for detecting the presence of these substances in engine oil.

Water and engine coolant have dielectric constants of approximately 87.5 and 37.9, respectively, and fuel has a dielectric constant of about 2.0. Therefore the introduction of such contaminants can significantly change the dielectric constant of the fluid which circulates through the engine for the purpose of lubrication. As a result, a condition of engine oil contamination could be mistaken for severe engine oil deterioration or vice versa.

The dielectric constant of oil is also influenced by the temperature of the oil and by the specific formulation of a given brand of oil.

SUMMARY OF THE INVENTION

Accordingly, an object of the present invention is to provide a combined oil quality and viscosity sensing system which distinguishes between the conditions of engine oil deterioration and contamination and provides separate indications of these conditions.

Another object is to provide a combined oil quality and viscosity sensing system which utilizes a combination of capacitive sensors to provide an indication of engine oil breakdown for a wide variety of engine oil conditions.

Another object is to provide a combined oil quality and viscosity sensing system which adjusts the engine oil measurements to compensate for the effects of engine oil temperature changes.

The related art in the field discusses the use of a capacitive sensors to determine oil deterioration and contamination. U.S. Pat. No. 5,824,889, issued to Dr. Kyong Park and assigned to Kavlico Corporation, discloses the use of a capacitive oil sensor to detect oil deterioration and contamination. U.S. Pat. No. 5,540,086, also issued to Dr. Park and assigned to Kavlico, discloses an oil deterioration sensor. U.S. Pat. No. 4,227,419, also issued to Dr. Park and assigned to Kavlico, discloses a capacitive pressure transducer. The foregoing patents of Dr. Park, one of the co-inventors in the present case, are hereby incorporated by reference into this specification.

In a specific illustrative preferred embodiment of the present invention, oil enters an internal combustion engine through a path and passes through a first pressurized port. The oil pressure is measured at the first pressurized port, and then flows through the combined system through a network of conduit. In the combined system, the oil is exposed to a capacitive sensor for determining the dielectric constant of the oil. After exposure to the capacitive sensor, the oil continues to flow through the combined system, passing through a second pressurized port. The oil pressure is again measured at this pressurized port. The oil then flows out of the system through a second path and on to the rest of the internal combustion engine. In an alternative embodiment, the oil is also exposed to a temperature sensor while in the system for measuring the temperature of the oil. In yet another embodiment, oil pressure may be measured at only one point in the system for a measurement of viscosity of the oil.

The presence of gasoline or other fuel which may leak into the lubricating oil of an internal combustion engine may adversely affect the validity of dielectric measurements of oil quality. Thus, with gasoline having a dielectric constant of about 2.0, the addition of gasoline to the lubricating oil mentioned above would reduce the dielectric constant and would make the oil appear not to have deteriorated as much as has actually occurred. Conversely, the addition of a substance with a very high dielectric constant would increase the dielectric constant of the oil and would make the oil appear to have deteriorated much more than has actually occurred.

Accordingly, a system illustrating the principles of the invention includes a capacitive sensor for determining the dielectric constant of lubricating oil, and a viscosity measuring arrangement, which would indicate whether gasoline or other low viscosity substance is present in the lubricating oil. In a preferred system, a temperature sensor would also be included, as viscosity and dielectric constant measurements are affected by temperature.

In accordance with a specific illustrative embodiment of a combined oil quality and viscosity sensing system, the present invention includes a housing, a first capacitive plate mounted within the housing, a second capacitive plate, and an insulating material between the housing and first capacitive plate. The capacitive plates are mounted such that fluid including oil circulates within a gap between the first and second capacitive plates thereby defining a capacitive dielectric sensor. The respective capacitances provide an indication of the dielectric constant of the oil within the gap. It is further noted that one of the capacitive plates may be a part of the housing.

In one specific illustrative embodiment, the oil viscosity is determined by the difference in oil pressure being applied to the engine, for example by the oil pump, and the oil pressure following passage through a restricted path, with the capacitive dielectric sensor constituting a major restriction in the flow path. This difference in pressure may be determined by a differential pressure transducer, such as a capacitive pressure transducer; or alternatively the pressure at each point may be measured separately, and the pressure difference may be determined by electrically combining the signals, or by mathematical subtraction in an associated computer or microprocessor.

A system according to one illustrative embodiment of the invention may include a high pressure oil input port, a capacitive sensor coupled to receive the oil, and a low pressure output port, with oil from said high pressure port and from said low pressure port being applied to pressure sensing arrangements for determining the differential pressure. Electrical circuitry is provided for (1) determining the dielectric constant of the oil from the capacitance of said capacitive sensor; (2) determining viscosity from said pressure sensing arrangements; and (3) to indicate both the oil quality and whether there is fuel contamination.

In another aspect of the present invention, the oil quality and viscosity sensing system further includes a temperature sensitive resistive element thermally coupled to the circulating oil for providing a temperature adjustment to the indication of dielectric constant and viscosity, and circuitry utilizing the temperature to adjust both the dielectric constant and viscosity indications.

Consequently, in a preferred embodiment of the combined system described above, a user of the present invention may introduce new oil to an internal combustion engine and receive an initial indication of oil quality and fuel contamination. Thereafter, subsequent readings over time would provide the user with information concerning the progression of any changes in oil quality as well as fuel contamination. The change in dielectric constant and pressure over time allows the user to detect a cause for oil deterioration and proceed accordingly. The addition of a temperature sensor allows a user of this embodiment to add further detail to the analysis of the condition of the lubricant within an engine.

DETAILED DESCRIPTION OF THE PREFERRED EMBODIMENTS

Figure 1:
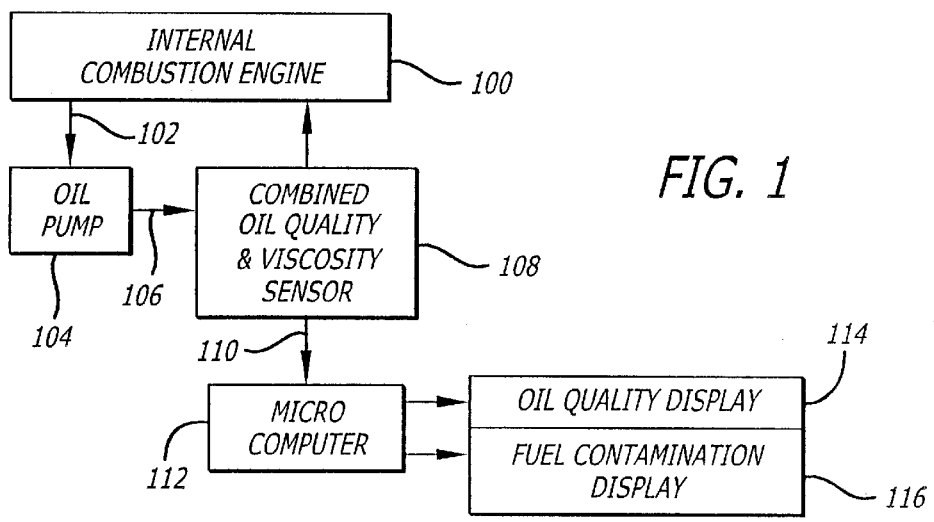
FIG. 1 is a block diagram overview of an illustrative embodiment of the invention and related components, showing the combined oil quality and viscosity sensing system coupled to an internal combustion engine, oil pump, microcomputer, and oil quality and fuel contamination display.

Referring more particularly to the drawings, FIG. 1 shows a block diagram overview of the combined oil quality and viscosity sensing system 108 and its relationship to other engine and system components. Oil flows from oil pump 104 through sensing system 108 and through internal combustion engine 100. The sensing system 108 produces output signals through electrical circuitry 110 to microcomputer 112, which shows oil quality on oil quality display 114 and fuel contamination level on fuel contamination display 116.

The oil quality and viscosity sensing system and the oil pump are coupled to the internal combustion engine 100 by conduits 102. Oil flows through the overall system through fluid delivery conduit 106 and passes the capacitive components of the oil quality and viscosity sensing system. The system then generates output electrical signals 110 to the microcomputer 112 and on to the displays 114 and 116.

Figure 2:
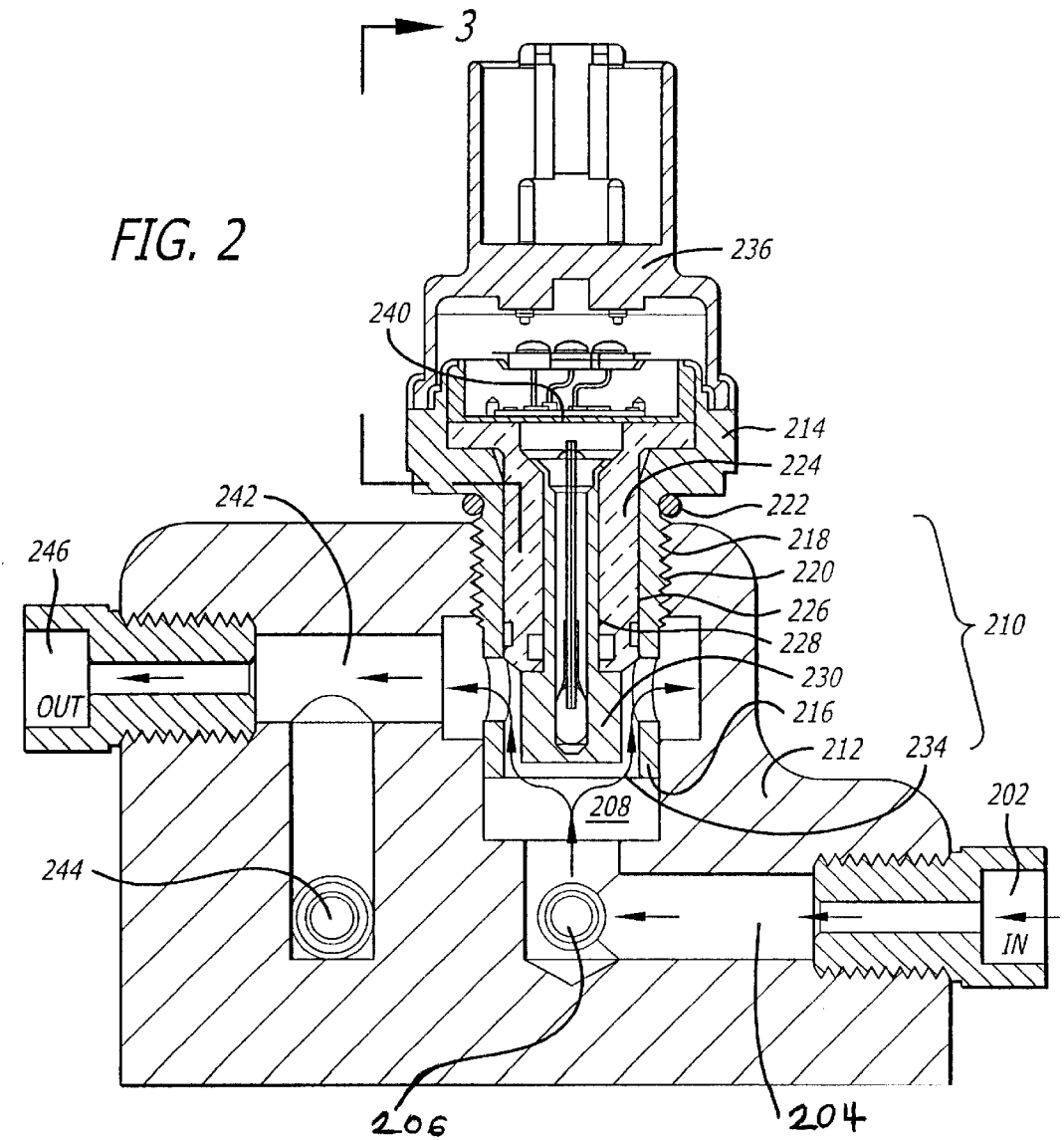
FIG. 2 is a cross-sectional side view of the combined oil quality and viscosity sensing system, showing the various components of the system, including the high and low pressure ports, the restricted paths, the pressure sensing arrangement, the capacitive dielectric sensor and temperature sensor.

FIG. 2 is cross sectional side view of a combined oil quality and viscosity sensing system. Motor oil enters the coupling 202 from an oil pump, and passes through conduit 204 to high pressure port 206. The motor oil then passes through conduit 208, and passes capacitive dielectric sensor 210. The oil continues to flow through the restricted path including conduit 208 and conduits 242 and sensor 210 and then passes low pressure port 244. The oil then exits the sensing system by way of coupling 246 and, following flow through the internal combustion engine, is recycled for subsequent use in said system.

In this view, capacitive dielectric sensor 210 is fitted within a housing 212. The sensor 210 includes a metal member 214 with a lower end 216 forming one of the capacitive plates. The member 214 preferably includes a threaded surface portion 218 which is fitted within a corresponding threaded bore 220 of the housing 212. A circular gasket 222 or o-ring made of a sealant such as rubber may also be positioned between the member 214 and the housing 212 as shown in FIG. 2.

The member 214 and particularly the lower end 216, are precisely machined to receive an insulating material 224. The preferred lower end 216 is sized to form a cylindrical chamber along the length of sensor 210. Accordingly, the preferred insulating material 224 is cylindrical in shape with an outer diameter slightly less than the inner diameter of the lower end 216. The insulating material 224 is preferably manufactured from material which efficiently conducts heat. For example, the insulating material 224 may be formed from a ceramic material such as alumina.

The insulating material 224 includes an outer surface 226 and an inner surface 228 on opposing sides thereof. The insulating material 224 provides insulation between the housing and two capacitive plates, one of which is the lower end 216 of the member 214, and the other being the lower exposed end of conductive member 230.

Engine oil freely circulates within a gap 234 between the two capacitive plates identified above. Accordingly, an oil deterioration and contamination sensor capacitor is defined by the first capacitive plate formed by the lower end of conductive member 230, the second capacitive plate formed by the lower end 216 of member 214, and the engine oil in the gap between these electrodes. The capacitance of the oil deterioration and contamination sensor capacitor varies depending upon the dielectric constant of the oil between the two electrodes.

The sensor 210 additionally includes a connector shell portion 236 which is mechanically connected to the member 214 as shown in FIG. 2. A plurality of connectors or conductive material terminals are secured within the shell portion 236.

The oil deterioration sensor 210 further includes circuitry within the member 214 for generating an engine oil deterioration indication output signal. Preferably, some of the elements of the circuitry are provided in an integrated circuit 240 (e.g. a hybrid integrated circuit) which is thermally isolated from the insulating material 224.

Reference is also made again to U.S. Pat. 5,824,889 to Dr. Kyong Park, which is herein incorporated by reference. The '889 patent teaches a capacitive oil deterioration and contamination sensor that measures dielectric constant. When combined with pressure sensing arrangements as described herein, the present invention allows for measurement of both dielectric constant of oil in a system as well as the viscosity of the oil.

Figure 3:
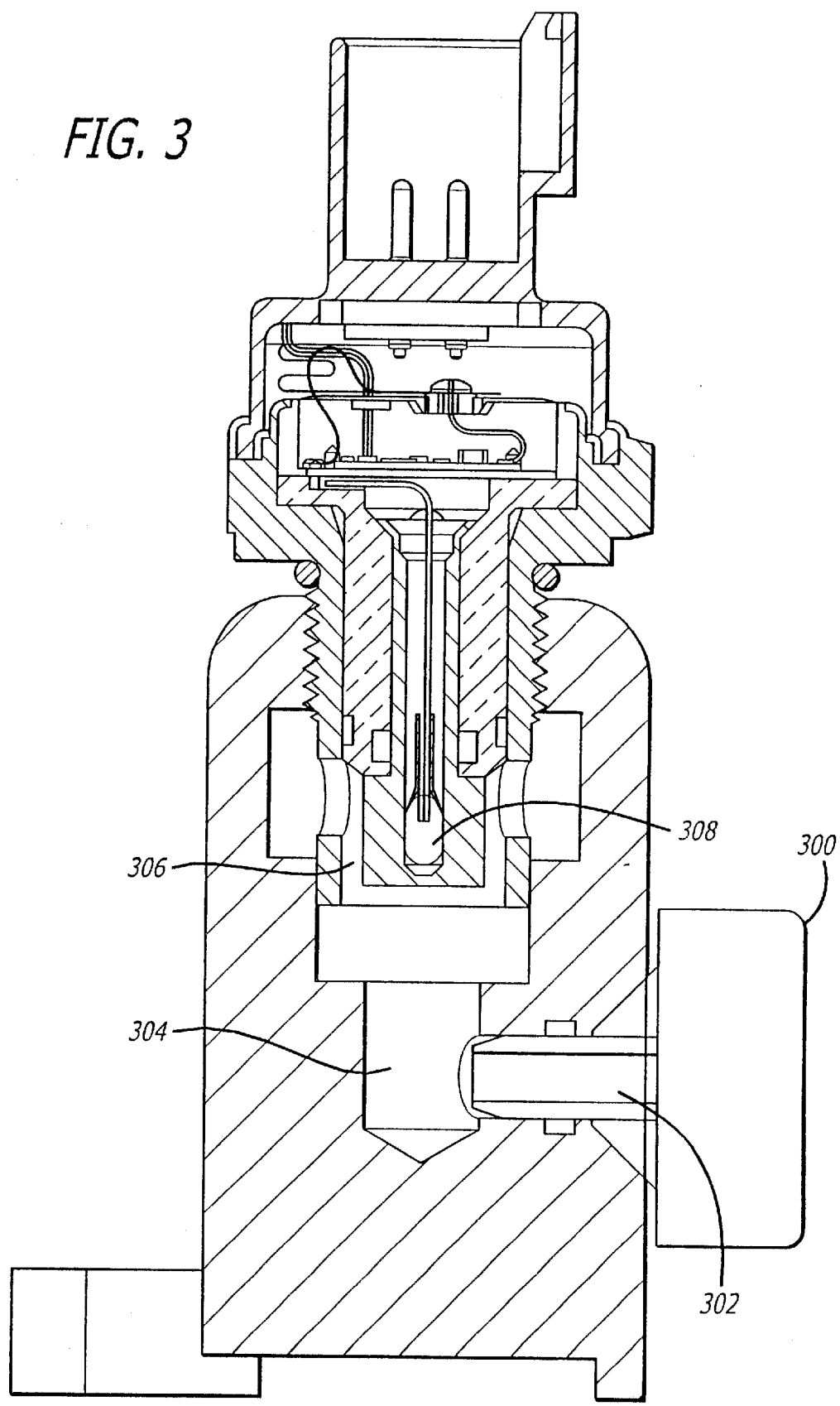
FIG. 3 is a cross-sectional side view of the combined oil quality and viscosity sensing system, showing the dielectric and temperature sensing components of the system as well as the pressure sensing arrangements.

FIG. 3 is a detailed cross sectional side view showing the sensing parts of the overall system. In this embodiment, oil passes pressure sensing arrangement 300, and moves through conduit 302. Pressure sensing arrangement 300 consists of a differential pressure transducer measuring pressure in the oil and outputting data via signals to the microprocessor. Once the oil is in the conduit 302, it enters fluid delivery conduit 304 where its dielectric constant is measured by capacitive sensor 306. The oil then flows out of the system through a conduit not shown in this Figure.

With further reference to FIG. 2 of the drawings, it may be noted that, between the high pressure port 206 and the low pressure port 244, the principal restriction in the flow path is provided by the capacitive dielectric sensor 210, with the conduit 208 coupling the low pressure port 206 to the sensor 210, and the conduit 243 coupling the output from the sensor 210 to the low pressure port 244.

In another preferred embodiment, the temperature of the motor oil is sensed by the temperature sensor 308. The oil follows the same exit as above, flowing through conduit 304 and out of the system after its attributes are measured by all sensors. It is noted in passing that the device of U.S. Pat. No. 5,824,889, issued to Dr. Kyong Park and incorporated herein by reference, may be combined with a temperature sensor as well as pressure sensing arrangements. The present invention may thus include a temperature sensor in addition to the dielectric sensor of the '889 patent.

With reference to FIG. 3, the motor oil is exposed to pressure sensing arrangement 300. The arrangement 300 may consist of two pressure sensors, or a single differential pressure sensor, measuring the pressure of the oil at different points within said system and sending the pressure data via output signals to the microprocessor. The pressure sensor 300 is coupled to both the high pressure and low pressure ports of the system. Using this measurement, as well as the dielectric constant measurement, the microprocessor can determine whether the dielectric constant output is an accurate reflection of the quality of the oil or if contamination has artificially lowered or raised the dielectric constant and masked the deterioration of the oil within the system.

The pressure sensing arrangements 300 further include circuitry for generating output signals. These signals can be used to measure pressure of the oil, which can be used to indicate viscosity. Preferably, some of the elements of the circuitry are provided in an integrated circuit 240 (e.g. a hybrid integrated circuit) which may be thermally isolated from the pressure sensing arrangements.

In conclusion, it is to be understood that the foregoing detailed description and the accompanying drawings illustrate the principles of the invention. However, various changes and modifications may be employed without departing from the spirit and scope of the invention. Thus, by way of example and not of limitation, the viscosity could be measured roughly, using a single low pressure port, such as port 244, and a single pressure sensor. Accordingly, the present invention is not limited to the specific form shown in the drawings and described in detail hereinabove.

What is claimed is:

1. An oil quality and viscosity sensing assembly for indicating oil condition, said sensing assembly comprising:

a housing having a conduit therethrough defining a restricted oil flow path within said housing, said conduit having an entering threaded inlet and an exiting threaded outlet;

a high pressure port, said high pressure port being along said conduit and in proximity to said entering threaded inlet;

a low pressure port, said low pressure port being along said conduit and in proximity to said exiting threaded outlet;

a capacitive dielectric sensor fitted within said housing and at a location between said high and low pressure ports along said conduit, said capacitive dielectric sensor having an outer metal member having a threaded outer surface portion which fits within a threaded bore of the housing, said sensor having a pair of spaced electrodes defining gap between said electrodes through which oil flows during its passage through said conduit;

said capacitive dielectric sensor constituting the principal restriction in the flow path between said high pressure port and said low pressure port;

pressure sensing arrangements coupled to said high pressure port and to said low pressure port;

a connector shell portion connected to said metal member; and circuitry coupling said capacitive dielectric sensor and said pressure-sensing arrangements to a microprocessor coupled to a display, in order to provide an indication of oil quality.

2. The oil quality and viscosity sensing assembly of claim 1, wherein said pressure sensing arrangements comprise a differential pressure transducer configured to measure the difference in pressure at said ports.

3. The oil quality and viscosity sensing assembly of claim 1, wherein said metal member is fitted to receive an insulating material.

4. The oil quality and viscosity sensing assembly of claim 3, further comprising a conductive member fitted within and protruding from said insulating material.

5. The oil quality and viscosity sensing assembly of claim 4, wherein said conductive member is further comprised of a temperature sensor with circuitry coupling said temperature sensor to said microprocessor in order to consider oil temperature effects in said indications of oil quality.

6. The oil quality and viscosity sensing assembly of claim 1, wherein said indications of oil quality comprise determining an oil dielectric constant and/or viscosity.

7. The oil quality and viscosity sensing assembly of claim 1, wherein said indications of oil quality further comprise indications of fuel contamination.

8. A combined oil quality and viscosity sensing system including an oil pump for circulating lubricating oil to the engine, said system comprising:

a housing having a conduit therethrough, defining a restricted oil flow path within said housing, said conduit having an entering threaded inlet and an exiting threaded outlet;

a capacitive sensor for determining the dielectric constant of oil, said capacitive sensor being fitted within said housing and along said conduit, between said entering threaded inlet and said exiting threaded outlet, said capacitive sensor being included in and forming part of said restricted flow path;

a high pressure port along said conduit between said entering threaded inlet and said sensor, said conduit receiving oil under pressure and for circulating the oil past said capacitive sensor;

a low pressure port along said conduit between said exiting threaded outlet and said sensor for receiving the oil following transmission through said restricted path from said high pressure port;

said capacitive dielectric sensor constituting the principal restriction in the flow path between said high pressure port and said low pressure port;

pressure sensing arrangement coupled to said high pressure port and to said low pressure port;

pressure sensing arrangements;

said conduit applying oil from said high pressure port and from said low pressure port to said pressure sensing arrangements; and circuitry coupled to said capacitive sensor and to said pressure sensing arrangements for indicating the oil quality and whether contamination is present in the oil.

9. A combined oil quality and viscosity sensing assembly, including an oil pump for circulating lubricating oil, said assembly comprising:

a housing having a conduit therethrough defining a restricted oil flow path within said housing, said conduit having an entering threaded inlet and an exiting threaded outlet;

a capacitive dielectric sensor located along said conduit and intervening between said entering threaded inlet and said exiting threaded outlet, said capacitive dielectric sensor comprised of an outer metal member having a threaded outer surface portion which fits within a threaded bore of the housing;

a low pressure port located between said sensor and said exiting outlet;

said capacitive dielectric sensor constituting the principal restriction in the flow path between said entering inlet and said low pressure port;

pressure sensing arrangements coupled to said low pressure port; and said conduits circulating oil past said capacitive dielectric sensor and said low pressure port.

10. The combined oil quality and viscosity sensing assembly as described in claim 8, wherein said pressure sensing arrangements comprise a differential pressure transducer configured to measure the difference in pressure within said system.

11. The combined oil quality and viscosity sensing assembly as described in claim 9, further comprising a microprocessor adapted to receive output signals from said capacitive dielectric sensor and said pressure sensing arrangements.

12. The combined oil quality and viscosity sensing assembly as described in claim 11, wherein said output signals indicate oil quality and level of fuel contamination within said internal combustion engine.

13. The combined oil quality and viscosity sensing assembly as described in claim 9, further comprising a temperature sensor for measuring the temperature of said oil.

14. A combined oil quality and viscosity sensing system including an oil pump for circulating lubricating oil to the engine, said system comprising:

a capacitive dielectric sensor for determining the dielectric constant of oil;

a high pressure port and conduit receiving oil under pressure and for circulating the oil past said capacitive sensor;

a low pressure port for receiving the oil following transmission through a restricted flow path from said high pressure port;

pressure sensing arrangements;

conduits for applying oil from said high pressure port and from said low pressure port to said pressure sensing arrangements;

said capacitive dielectric sensor constituting the principal restriction in said restricted flow path; and circuitry coupled to said capacitive sensor and to said pressure sensing arrangements for indicating the oil quality and whether contamination is present in the oil.

15. The combined oil quality and viscosity sensing system as described in claim 14, wherein said pressure sensing arrangements comprise a differential pressure transducer configured to measure the difference in pressure at said ports.

16. The combined oil quality and viscosity sensing system as described in claim 1, further comprising a microprocessor coupled to receive output signals from said dielectric capacitive sensor and said pressure sensing arrangements.

17. The combined oil quality and viscosity sensing system as described in claim 16, wherein a display is coupled to said microprocessor to indicate the dielectric constant of oil and contamination of the oil within said internal combustion engine.

* * * * *